United States Patent
Herzig et al.

(10) Patent No.: US 6,252,101 B1
(45) Date of Patent: Jun. 26, 2001

(54) ORGANOSILICON COMPOUNDS CONTAINING ALKENYL GROUPS

(75) Inventors: Christian Herzig, Waging am See; Bernward Deubzer, Burghausen; Johann Weis, Sauerlach; Kamelia Karlou-Eyrisch; Oskar Nuyken, both of München, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/261,823

(22) Filed: Mar. 3, 1999

(30) Foreign Application Priority Data

Mar. 5, 1998 (DE) .............................................. 198 09 551

(51) Int. Cl.$^7$ ...................................................... C07F 7/08
(52) U.S. Cl. .............................................................. 556/453
(58) Field of Search .............................................. 556/453

(56) References Cited

U.S. PATENT DOCUMENTS

5,264,606   11/1993   Moloy et al. .

FOREIGN PATENT DOCUMENTS

41 28 932 A1   3/1993   (DE) .

OTHER PUBLICATIONS

Polymer. Repr. 33 (1), 1078 (Wagener, Smith), Acyclic Diene Metathesis (ADMET) Polymerization, Synthesis of Unsaturated Poly9carbosilixanes), 1992.
J. Organomet. Chem. 447, (1993) 2, 163–166 (Marciniec).
Angew. Chem. 1997, 109 (3), 257–259 9Schneider et al.)
Chemical Abstract 126:237970, 1997.
Polym. Prepr. 35(1), 688 (1994).
Abstract (93–077647[14]) corresponding to DE 41 28 932, 1993.
Appl. Organomet. Chem. 1997, 11 (8), 667–671 (Marciniec).
Derwent Abstract corr. to DE 41 28 932, 1993.
Finkelshtein, E. Sh. et al., Olefin Metathesis in Organosilicon Chemistry, 1998, vol. 506, pp. 201–224.
Finkelshtein, E. Sh. et al., Ring–opening Metathesis Polymerization of Norbornenes with Organosilicon Substituents, 1991, vol. 192, pp. 1–9.

Primary Examiner—Paul F. Shaver
(74) Attorney, Agent, or Firm—Brooks & Kushman P.C.

(57) ABSTRACT

The invention describes new organosilicon compounds containing alkenyl groups, comprising units of the formula $$A_a R_b (R^1 O)_c SiO_{\frac{4-(a+b+c)}{2}}, \quad (I)$$

where R are identical or different and are each a monovalent hydrocarbon radical which is free of aliphatic carbon-carbon multiple bonds, has from 1 to 20 carbon atom(s) per radical and may contain from 1 to 4 oxygen atom(s),
$R^1$ are identical or different and are each a monovalent hydrocarbon radical which is free of aliphatic carbon-carbon multiple bonds and has from 1 to 8 carbon atom(s) per radical,
a is 0 or 1,
b is 0, 1, 2 or 3,
c is 0, 1, 2 or 3, preferably 0, where the sum a+b+c≦3,
A is a radical of the formula $$-(R^2)_d-Y(-CH=CHR^3)_2$$

where $R^2$ is a divalent hydrocarbon radical which is free of aliphatic carbon-carbon multiple bonds and has from 1 to 6 carbon atom(s),
$R^3$ are identical or different and are each a hydrogen atom or are as defined for R,
Y is a trivalent hydrocarbon radical which has from 2 to 20 carbon atoms and may contain from 1 to 4 oxygen atom(s) and d is 0 or 1,
with the proviso that the organosilicon compounds have at least two units of the formula (I) and at least one radical A per molecule.

25 Claims, No Drawings

ORGANOSILICON COMPOUNDS CONTAINING ALKENYL GROUPS

BACKGROUND OF THE INVENTION

In Polym. Repr. 33 (1), 1078, Wagener and Smith describe ring-closure reactions of olefinic Si compounds in which ethylene is eliminated. For example, 1,3-diallyldisiloxanes are cyclized to form unsaturated 7-membered rings and siloxanes containing relatively long 1-alkenyl radicals are polymerized.

Similar coupling reactions are known from J. Organomet. Chem. 447 (1993) 2, 163–166 (Marciniec) and Appl. Organomet. Chem. 1997, 11 (8), 667–671 (Marciniec). Here, silanes having terminal double bonds, e.g. Si-bonded vinyl groups, are reacted with other olefins. The products obtained are not reactive in hydrosilylation reactions.

According to Angew. Chem. 1997, 109 (3), 257–259 (Schneider et al.) or the corresponding Chemical Abstract 12 237970, allyltrimethylsilane is used as ring-opening reagent for cycloolefins, forming silanes having a terminal C=C group.

U.S. Pat. No. 5,264,606 (Union Carbide Chemicals & Plastics Technology Corporation, issued on Nov. 23, 1993) describes a process for preparing monomeric polyvinyl compounds and their oligomers by heterogeneously catalyzed cross-metathesis of norbornene or substituted norbornenes such as 5-triethoxysilyl-2-norbornene with ethylene in the presence of activated rhenium oxide fixed-bed catalysts.

DISCLOSURE OF THE INVENTION

It is an object of the invention to provide organosilicon compounds containing alkenyl groups which can be prepared in a simple process which uses readily available starting materials and allows two terminal alkenyl groups to be introduced on one Si atom. These and other objects are achieved by the invention.

DESCRIPTION OF THE PREFERRED EMBODIMENTS

The invention provides organosilicon compounds containing alkenyl groups and comprising units of the formula $$A_a R_b (R^1 O)_c SiO_{\frac{4-(a+b+c)}{2}}, \quad (I)$$

where R are identical or different and are each a monovalent hydrocarbon radical which is free of aliphatic carbon-carbon multiple bonds, has from 1 to 20 carbon atom(s) per radical and may contain from 1 to 4 oxygen atom(s),
$R^1$ are identical or different and are each a monovalent hydrocarbon radical which is free of aliphatic carbon-carbon multiple bonds and has from 1 to 8 carbon atom(s) per radical,
a is 0 or 1,
b is 0, 1, 2 or 3,
c is 0, 1, 2 or 3, preferably 0, where the sum a+b+c<3,
A is a radical of the formula $$-(R^2)_d-Y(-CH=CHR^3)_2$$

where $R^2$ is a divalent hydrocarbon radical which is free of aliphatic carbon-carbon multiple bonds and has from 1 to 6 carbon atom(s),
$R^3$ are identical or different and are each a hydrogen atom or are as defined for R, Y is a trivalent hydrocarbon radical which has from 2 to 20 carbon atoms and may contain from 1 to 4 oxygen atom(s) and d is 0 or 1,
with the proviso that the organosilicon compounds have at least two units of the formula (I) and at least one radical A per molecule.

The invention further provides a process for preparing organosilicon compounds containing alkenyl groups, which comprises reacting organosilicon compounds (1) comprising units of the formula $$B_a R_b (R^1 O)_c SiO_{\frac{4-(a+b+c)}{2}}, \quad (II)$$

where R, $R^1$ a, b and c are as defined above,
B is a radical of the formula

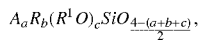

$R^2$, Y and d are as defined above,
with the proviso that the organosilicon compounds have at least two units of the formula (II) and at least one radical B per molecule,
with α-olefins (2) of the formula $R^3$—CH=CH$_2$ in the presence of metathesis catalysts (3) selected from the group consisting of transition metal compounds or complexes of transition groups IV to VIII of the Periodic Table.

The novel organosilicon compounds containing alkenyl groups preferably have a viscosity of from 1 to 10,000 at 25° C., more preferably from 1 to 500 at 25° C. and particularly preferably from 1 to 50 at 25° C.

The novel organosilicon compounds containing alkenyl groups preferably contain at least two radicals A, more preferably from 2 to 5 radicals A and particularly preferably from 2 to 3 radicals A.

The novel organosilicon compounds containing alkenyl groups are preferably oligomeric and polymeric organopolysiloxanes.

Examples of radicals R are alkyl radicals such as the methyl, ethyl, n-propyl, iso-propyl, n-butyl, iso-butyl, tert-butyl, n-pentyl, iso-pentyl, neo-pentyl and tert-pentyl radicals, hexyl radicals such as the n-hexyl radical, heptyl radicals such as the n-heptyl radical, octyl radicals such as the n-octyl radical and iso-octyl radicals such as the 2,2,4-trimethylpentyl radical, nonyl radicals such as the n-nonyl radical, decyl radicals such as the n-decyl radical, dodecyl radicals such as the n-dodecyl radical and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radicals, alkaryl radicals such as o-, m-, p-tolyl radicals, xylyl radicals and ethylphenyl radicals, and aralkyl radicals such as the benzyl radical, the α- and the β-phenylethyl radicals. Preference is given to the methyl radical.

Examples of radicals $R^1$ are alkyl radicals having from 1 to 8 carbon atom(s), e.g. the methyl, ethyl, n-propyl, iso-propyl, 1-n-butyl, 2-n-butyl, iso-butyl and tert-butyl radicals. Preference is given to the methyl and ethyl radicals. Examples of alkyl radicals $R^1$ which are substituted by an oxygen atom are the methoxyethyl and ethoxyethyl radicals.

Examples of radicals $R^2$ are those of the formulae
—H$_2$—,

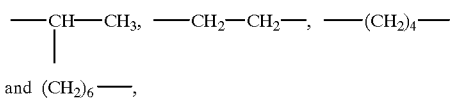

with preference being given to radicals of the formulae

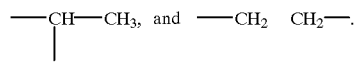

R³ is preferably a hydrogen atom.
Examples of radicals Y are the
1,2,4-butanetriyl radical,
1,3,6-hexanetriyl radical,
1,2,4-cyclopentanetriyl radical and the 2-methylenyl-3,5-bicyclo[2.2.1]heptanediyl radical of the formula

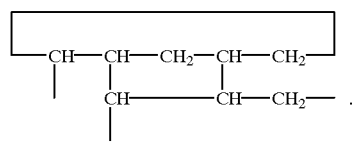

Examples of radicals A are the
4-(1,7-octadienyl),
5-(1,9-decadienyl),
2-(2,4-divinylcyclopentyl)ethyl,
2,4-divinylcyclopentyl and
2(4)-vinyl-4(2)-l-octenyl radicals.
Examples of radicals B are the
3-cyclohexenyl,
4-cyclooctenyl,
5-norbornenyl,
2-(5-norbornenyl)ethyl and 2(3)-dicyclopentadienyl radicals.
Examples of α-olefms (2) are ethylene, 1-octene, 1-pentene, 1-hexene, 1-dodecene, preference being given to ethylene.

Methods of preparing the organosilicon compounds (1) are known to those skilled in the art. 2-(norbornenyl)ethylsiloxanes are obtainable, for example, by hydrosilylation of 5-vinylnorbornene using organo(poly)siloxanes containing Si-bonded hydrogen, and 5-norbornenylsiloxanes are obtainable by analogous reactions from norbornadiene, as described in DE-A 41 28 932 (Wacker-Chemie GmbH, published on Mar. 4, 1993).

In the process of the invention, the ratio of α-olefins (2) to radicals B in organosilicon compound (1) is preferably from 1:1 to 20:1.

The metathesis catalysts (3) used in the process of the invention can be the same catalysts as have hitherto proven useful in metathesis reactions.
Examples of transition metal catalysts are compounds of titanium, tungsten, molybdenum and ruthenium, with particular preference being given to those of ruthenium.
The process of the invention can be carried out in the presence of homogenous or heterogeneous catalysts. It is preferably carried out in the presence of homogeneous catalysts.
In the case of the homogeneous systems, a distinction is made between single-component and multicomponent catalysts. The multicomponent catalysts preferably comprise transition metal compounds or complexes of transition groups IV to VII of the Periodic Table and a cocatalyst, and if desired, an oxygen-containing promoter. The complexes can contain halogen atoms and/or carbonyl groups and/or nitrosilyl groups. Examples are:

WCl$_6$/SnMe$_2$Et$_2$O,
W(CO)$_5$(PPh$_3$)/O$_2$/EtAlCl$_2$ and
MoCl (NO) (CO)$_2$ (PPh$_3$)/EtAlCl$_2$ (Me=methyl, Ph=phenyl).

Further examples of multicomponent catalysts are transition metal complexes with diazoalkane cocatalysts:

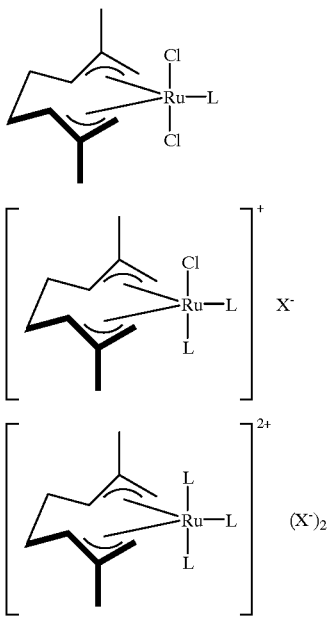

L=NCMe$_2$NCPh, PPh$_3$, P(OiPr)$_3$, P(Cy)$_3$, 3-Me-pyridine (Me=methyl, Ph=phenyl, iPr=iso-propyl, Cy=cyclohexyl).
X=BF$_4$, F$_3$CSO$_3$,
cocatalyst: N$_2$CHSiMe$_3$ or N$_2$CHCOOEt.

As single-component catalyst, use is preferably made of transition metal carbene complexes of transition groups IV to VIII. An example is the Schrock catalyst:

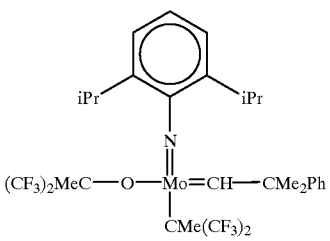

where Me=methyl radical, Ph=Phenyl radical, and iPr=iso-propyl radical.

A preferred example of a multicomponent catalyst is a ruthenium-carbene complex which can be prepared from the dimeric bisallylic ruthenium complex, tricyclohexylphosphine and trimethylsilyldiazomethane:

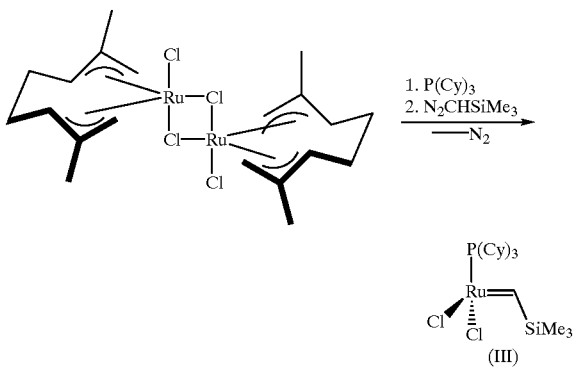

A preferred example of a single-component catalyst is a ruthenium-carbene complex of the Grubbs type (Polym. Prepr. 35 (1), 688 (1994)) of the formula:

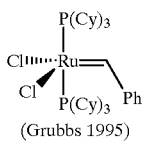
(Grubbs 1995)

$RuCl_2$ (=CHPh)(PCy$_3$)$_2$, where
Cy is a Cyclohexyl Radical.

This single-component catalyst has a high cross-metathesis activity and a long operating life. It is soluble both in polar solvents and nonpolar solvents, e.g. methanol or n-hexane. Owing to the higher solvent capability for ethylene, nonpolar solvents such as toluene and n-hexane are preferred.

A further preferred catalyst is a ruthenium complex of the formula $RuCl_2$ (=CH—CH=CPh$_2$) (PCy$_3$)$_3$, where
Ph is the phenyl radical, and Cy is the cyclohexyl radical.

In the process of the invention, the molar ratio of transition metal in the metathesis catalyst (3) to radicals B in the organosilicon compound (1) is preferably from 1:100 to 1:100,000, particularly preferably from 1:500 to 1:5000.

The process of the invention is preferably carried out at the pressure of the surrounding atmosphere, i.e. at about 1020 hPa (abs.). However, it can also be carried out at higher or lower pressures. Furthermore, the process of the invention is preferably carried out at a temperature of from −20° C. to 100° C., more preferably from 0C to 80° C., particularly preferably from 10° C. to 50° C.

A preferred example of the process of the invention is the reaction of organosilicon compound (1) with 1-octene in the presence of the multicomponent ruthenium catalyst of the formula (III). The molar ratio of ruthenium in the ruthenium catalyst of the formula (III) to radicals B in the organosilicon compound (1) is preferably from 1:100 to 1:10,000, particularly preferably 1:500. The molar ratio of 1-octene to radicals B in the organosilicon compound (1) is preferably from 1.5:1 to 10:1, particularly preferably 3:1. The cross-metathesis reaction is preferably carried out at a temperature of from −10C to 80° C., particularly preferably from 25° C. to 30° C.

The cross-metathesis reaction with ethylene is preferably carried out using the stable single-component ruthenium catalyst of the formula (IV). A preferred example of the process of the invention is therefore the reaction of organosilicon compound (1) with ethylene in the presence of the single-component ruthenium catalyst of the formula (IV). The molar ratio of ruthenium in the ruthenium catalyst of the formula (IV) to radicals B in the organosilicon compound (1) is preferably from 1:100 to 1:10,000, particularly preferably from 1:2000 to 1:8000. The molar ratio of ethylene to radicals B in the organosilicon compound (1) is preferably from 1:1 to 50:1, particularly preferably from 1:1.5 to 1:15. The cross-metathesis reaction is preferably carried out at a temperature of from −20° C. to 80° C., particularly preferably at 40° C.

Inert organic solvents can be used in the process of the invention. Examples of inert organic solvents are toluene, n-hexane, methanol, butanol, tetrahydrofuran or distillation fractions of hydrocarbons with boiling points or ranges up to about 200° C.

Before the work-up of the mixture obtained in the process of the invention, the metathesis catalyst (3) can be deactivated. Excess α-olefin (2) and any inert organic solvent used are preferably removed by distillation from the organosilicon compounds containing alkenyl groups prepared by the process of the invention.

The organosilicon compounds containing alkenyl groups obtained by the process of the invention can, if desired, subsequently be equilibrated with organopolysiloxanes (4). As organopolysiloxanes (4), preference is given to ones selected from the group consisting of linear, triorganosiloxy-terminated organopolysiloxanes of the formula $R_3SiO(R_2SiO)_rSiR_3$, where R is as defined above and
r is 0 or an integer from 1 to 1000, preferably from 100 to 400, and linear, hydroxyl-terminated organopolysiloxanes of the formula $HOR_2SiO(SiR_2o)_rSiR_2OH$, where R and r are as defined above.

The ratio of the organopolysiloxanes (4) used in any equilibration carried out to organosilicon compounds containing alkenyl groups is determined only by the desired proportion of alkenyl groups in the organopolysiloxanes produced in the equilibration and by the desired mean chain length.

In the equilibration which may be carried out, preference is given to using basic or acid catalysts which promote the equilibration. Examples of basic catalysts are alkali metal hydroxides such as sodium hydroxide and potassium hydroxide, trimethylbenzylammonium hydroxide and tetramethylammonium hydroxide. Preference is given to alkali metal hydroxides. Alkali metal hydroxides are preferably used in amounts of from 50 to 10,000 ppm by weight (=parts per million), in particular from 500 to 2000 ppm by weight, in each case based on the total weight of the organosilicon compounds containing alkenyl groups used and organopolysiloxanes (4) used.

Examples of acid catalysts are sulfuric acid, phosphoric acid, trifluoromethanesulfonic acid, phosphonitrilic chlorides and acid catalysts which are solid under the reaction conditions, e.g. acid-activated bleaching earth, acid zeolites, sulphonated carbon and sulphonated styrene-divinylbenzene copolymer. Preference is given to phosphonitrilic chlorides. Phosphonitrilic chlorides are preferably used in amounts of from 5 to 1000 ppm by weight (=parts per million), in particular from 50 to 200 ppm by weight, in each case based on the total weight of the organosilicon compounds containing alkenyl groups used and organopolysiloxanes (4) used.

The equilibration which may be carried out is preferably carried out at from 100° C. to 150° C. and at the pressure of the surrounding atmosphere, i.e. at about 1020 hPa (abs.). However, if desired, higher or lower pressures can also be employed. The equilibration is preferably carried out in from 5 to 20% by weight, based on the total weight of the organopolysiloxanes containing aliphatically unsaturated hydrocarbon radicals and organopolysiloxanes (5) used, of a water-immiscible solvent such as toluene. Before the work-up of the mixture obtained in the equilibration, the catalyst can be deactivated.

The process of the invention can be carried out batchwise, semicontinuously or fully continuously.

The novel organosilicon compounds containing alkenyl groups can be used in hydrosilylation reactions.

EXAMPLE 1

Reaction of 5-norbornenylpentamethyldisiloxane with 1-octene
Reaction Equation:

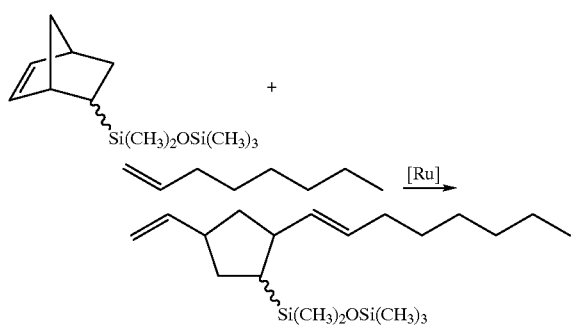

A Mixture of Cis And Trans Isomers
Reagent Ratio:
[Ru]/[cycloolefin]=1/600;[1-octene]/[cycloolefin]=2.4

1.12 g (0.01 mol) of 1-octene in 12 ml of toluene are placed under argon in a 100 ml Schlenk flask. To prepare the ruthenium catalyst of the formula (III) in situ, $4.3 \cdot 10^{-3}$ g ($0.7 \cdot 10^{-5}$ mol) of the corresponding dimeric bisallylic ruthenium(IV) complex are dissolved in 2 ml of toluene. The solution is admixed with $7.9 \cdot 10^{-3}$ g ($2.8 \cdot 10^{-5}$ mol) of tricyclohexylphosphine (color change from violet to yellow) and added to the 1-octene solution. Immediately thereafter, 0.014 ml ($2.8 \cdot 10^{-5}$ mol) of trimethylsilyldiazomethane is added and a solution of 1 g ($4.2 \cdot 10^{-3}$ mol) of 5-norbornenylpentamethyl-disiloxane dissolved in 5 ml of toluene is then quickly added dropwise. The ratio of ruthenium catalyst to cycloolefin radical is 1:600, the ratio of 1-octene to cycloolefin radical is 2.4:1. After about 40 minutes, the reaction solution is treated with 0.01 ml of n-butyl vinyl ether to deactivate the catalyst. The reaction mixture is evaporated on a rotary evaporator (30° C. and 40 mbar). The deep green solution is admixed with 2 g of deactivated $Al_2O_3$. The solid is filtered off and washed a number of times with n-hexane. The filtrate is subsequently evaporated on a rotary evaporator and solvent residues are finally removed in a high vacuum. The product is obtained as a colorless, low-viscosity liquid. The yield is 0.97 g ($2.8 \cdot 10^{-3}$ mol, 66% of theory).

Analytical Data:
$C_{20}H_{40}OSi_2$ (352.35)
$^1H$—NMR (300 Mhz, $CDCl_3$): d=5.7(m,H), 5.5(bs,2H), 4.97–5.03 (m,2H), 2.19–2.2 (m,2H), 1.96 (m,2H), 1.51–1.52 (m,5H), 1.34 (m,2H), 1.29 (4H), 0.96 (3H), (9H), –0.1 (15H).
IR (film) n($cm^{-1}$): 3078(w), 2955 (s,C—H), 1639 (w,=CH), 1253 (s), 1063(s,SiO), 993(w) 908(m, RCH=$CH_2$), 840(s), 802–778 (m).
MS: m/e(%)=352($M^+$, 3), 337($M^+$—$CH_3$,4), 147 ($M^+$—$Cl_5H_{25}$).

EXAMPLE 2

Reaction of 2-(5-Norbornenyl)ethylpentamethyldisiloxane with ethylene
Reaction Equation:

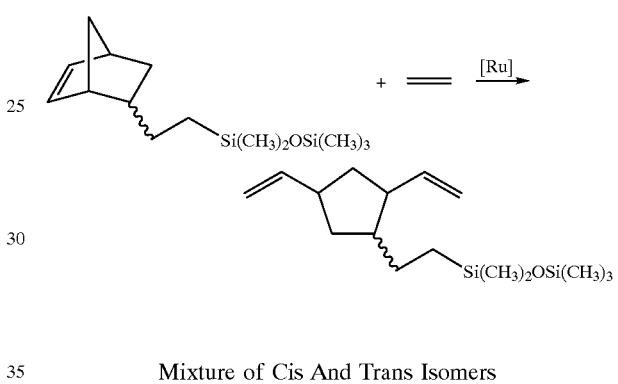

Mixture of Cis And Trans Isomers
Reagent Ratio:
[Ru]/[Cycloolefin]=1/2500;[ethylene]/[cycloolefin]=15

In a Buichi autoclave fitted with a 250 ml glass liner and an electric stirrer, $2.5 \cdot 10^{-3}$ g ($3.0 \cdot 10^{-6}$ mol) of the ruthenium catalyst of the formula $RuCl_2$(=CHPh)($PCy_3)_2$ (IV) are dissolved under argon in 100 ml of toluene (pale violet solution). While stirring vigorously, ethylene is passed into the autoclave at room temperature and a gauge pressure of 4 bar. After the solution has been saturated, the ethylene gas feed is shut off. 2 g (2 ml, $7.5 \cdot 10^{-3}$ mol) of 2-(5-norbornenyl)ethylpentamethyldisiloxane are dissolved in 5 ml of toluene and introduced under argon into the reservoir. The ratio of ruthenium catalyst to cycloolefin radical is 1:2,500, the ratio of ethylene to cycloolefin radical is 15:1. The cross-metathesis reaction is started by injecting the 2-(5-norbornenyl)-ethylpentamethyldisiloxane. After a reaction time of about 20 minutes, the overpressure is released and the reaction mixture is degassed while stirring. The work-up of the product follows as described in Example 1. This gives 1.86 g ($6.3 \cdot 10^{-3}$ mol, 84% of theory) of 2-(2,4-divinylcyclopentyl)ethylpentamethyldi-siloxane.

Analytical Data:
$C_{14}H_{28}OSi_2$(296.38)
$^1H$—NMR (300 MHz, $CDCl_3$): d=5.6–5.8 (m,2H), 4.8–4.95 (m,4H), 2.6 (ddt,1H), 2.45 (dt,IH), 1.7–1.9 (m,2H), 1.2–1.5 (m,3H), 0.95–1.05 (m,2H), 0.4 (m,2H), –0.1 (15H).
MS: m/e (%)=281 ($M^+$—$CH_3$,6), 253 (10.6), 147 (100), 133 (83), 73 (45.5).

EXAMPLE 3

Reaction of 1,3-bis(5-norbornenyl)-tetramethyldisiloxane with ethylene

Reaction Equation:

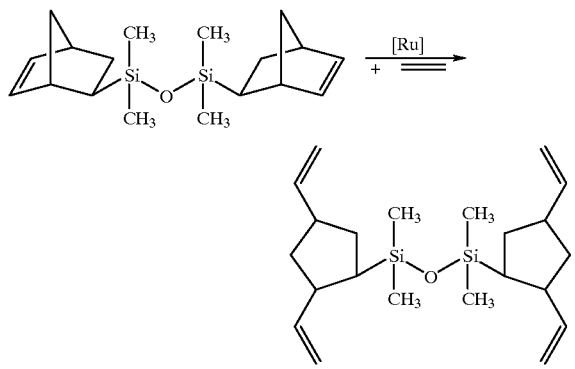

Reagent Ratio:

[Ru]/[cycloolefin]=1/8000; [ethylene]/[cycloolefin]=6

The reaction is carried out using a method analogous to Example 2. 200 ml of toluene, 4 bar (0.112 mol) of ethylene, $2 \cdot 10^{-3}$ g ($2.4 \cdot 10^{-6}$ mol) of ruthenium catalyst of the formula (IV) and 3 g ($9.4 \cdot 10^{-3}$ mol) of 1,3-bis(5-norbornenyl) tetramethyldisiloxane are used. The ratio of ruthenium catalyst to cycloolefin radical is 1:8000, the ratio of ethylene to cycloolefin radical is 6:1. This gives 2.7 g ($7.2 \cdot 10^{-3}$ mol, 77% of theory) of 1,3-bis(2,4-divinylcyclopentyl) tetramethyldisiloxane).

The $^1$H—NMR spectrum is free of signals of the bridgehead protons of the starting material 1,3-bis(5-norbornenyl) tetramethyldisiloxane at 3.0 ppm.

The secondary reaction of oligomerization is about 4%: C—CH=CH$_2$/C—CH=CH—C=23:1 compared to 12:1 for a purely random reaction. The reaction is about twice as selective as expected.

Analytical Data:

C$_{22}$H$_{38}$OSi$_2$(374.37)

$^1$H—NMR (300 MHz, CDCl$_3$): d=5.7–5.8 (m, 4H), 4.8–4.95 (m,8H), 2.85 (m,4H), 2.5 (m,4H), −0.1 (12H).

IR (film) n(cm$^{-1}$): 3076(w), 2950 (s, C—H), 2861 (m,C—H), 1639 (w,=CH), 1166(m), 1253 (s, —SiCH$_3$), 1062 (s,—SiO), 993(m), 908(s, RCH=CH$_2$), 781(s).

EXAMPLE 4

Reaction of α,ω-bis(5-norbornenyl)polydimethylsiloxane with ethylene

Reaction Equation:

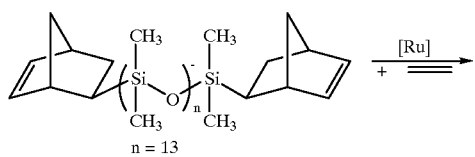

n = 13

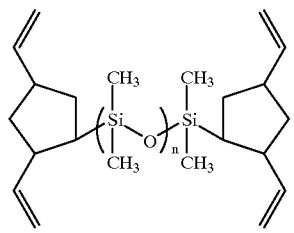

Reagent Ratio:

[Ru]/[cycloolefin]=1/4000; [ethylene]/[cycloolefin]=8

The reaction is carried out using a method analogous to Example 2. 400 ml of toluene, 2 bar (0.096 mol) of ethylene, $2.5 \cdot 10^{-3}$ g ($3 \cdot 10^{-6}$ mol) of ruthenium catalyst of the formula (IV) and 7 g ($5.8 \cdot 10^{-3}$ mol) of bis(5-norbornenyl) polydimethylsiloxane having an average chain length of 14.5 are used. The ratio of ruthenium catalyst to cycloolefin radical is 1:4000, the ratio of ethylene to cycloolefin radical is 8:1. This gives 6.6 g (90% of theory) of α,ω-bis(2,4-divinylcyclopentyl)polydimethylsiloxane.

The $^1$H—NMR spectrum is free of signals of the bridgehead protons of the starting material α,ω-bis(5-norbornenyl) polydimethylsiloxane at 2.9 ppm.

The extent of oligomerization is <0.9%:
C—CH=CH$_2$/C—CH=CH—C=116:1 compared to 16:1 for a purely random reaction. The reaction is about seven times as selective as expected.

Analytical Data:

$^1$H—NMR (300 MHZ, CDCl$_3$): d=5.7–5.8 (m,4H), 4.8–4.95 (m,8H), 2.85 (m,4H), 2.5(m,4H), −0.1 (84H).

IR (film) n(cm$^{-1}$): 3076(w), 2950 (s,C—H), 2861(m,C—H), 1639 (w,=CH), 1166(m), 1253(s, —SiCH$_3$), 1062 (s, —SiO), 993(m), 908 (s,RCH=CH$_2$), 781(s).

EXAMPLE 5

6.5 g of the α,ω-bis(2,4-divinylcyclohexyl) polydimethylsiloxane containing a total of 20 meq. of vinyl groups, whose preparation is described in Example 4, are mixed with 60 g of dimethylcyclosiloxane and heated to 140° C. The homogeneous siloxane mixture is catalyzed using 200 ppm of phosphonitrilic chloride and equilibrated at the same temperature for two hours. It is neutralized with 1 g of MgO and filtered, and volatile constituents are distilled off at 3 hPa/140° C. This gives 55 g of a clear silicone oil having two vinyl groups at each chain end.

The oil has a viscosity of 480 mm$^2$/s at 25° C. and an iodine number of 9.0.

What is claimed is:

1. An organosilicon compound containing alkenyl groups and comprising units of the formula $$A_a R_b (R^1 O)_c SiO_{\frac{4-(a+b+c)}{2}}, \quad (I)$$

where R are identical or different and are each a monovalent hydrocarbon radical which is free of aliphatic carbon-carbon multiple bonds, has from 1 to 20 carbon atom(s) per radical and optionally contains from 1 to 4 oxygen atom(s), $R^1$ are identical or different and are each a monovalent hydrocarbon radical which is free of aliphatic carbon-carbon multiple bonds and has from 1 to 8 carbon atom(s) per radical, a is 0 or 1, b is 0, 1, 2 or 3, c is 0, 1, 2 or 3, preferably 0, where the sum $a+b+c \leq 3$, A is a radical of the formula

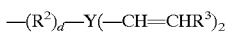
$$-(R^2)_d-Y(-CH=CHR^3)_2$$

where $R^2$ is a divalent hydrocarbon radical which is free of aliphatic carbon-carbon multiple bonds and has from 1 to 6 carbon atom(s), $R^3$ are identical or different and are each a hydrogen atom or are as defined for R, Y is a trivalent hydrocarbon radical which has from 2 to 20 carbon atoms and may contain from 1 to 4 oxygen atom(s) and d is 0 or 1, with the proviso that the organosilicon compound has at least two units of the formula (I) and at least one radical A per molecule.

2. A process for preparing organosilicon compounds containing alkenyl groups as claimed in claim 1, which comprises reacting organosilicon compounds (1) comprising units of the formula

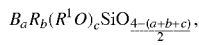
$$B_a R_b (R^1O)_c SiO_{\frac{4-(a+b+c)}{2}}, \quad (II)$$

where R, $R^1$ a, b and c are as defined above,

B is a radical of the formula

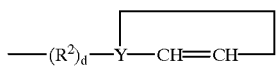
$$-(R^2)_d-Y-CH=CH-$$

where $R^2$, Y and d are as defined above, with the proviso that the organosilicon compounds have at least two units of the formula (II) and at least one radical B per molecule, with α-olefins (2) of the formula $R^3-CH=CH_2$ in the presence of at least one metathesis catalyst (3) selected from the group consisting of transition metal compounds or complexes of transition groups IV to VIII of the Periodic Table.

3. The process as claimed in claim 2, wherein the reaction is homogeneously catalyzed.

4. The process as claimed in claim 2, wherein the metathesis catalyst (3) used comprises a ruthenium complex.

5. The process as claimed in claim 3, wherein the metathesis catalyst (3) used comprises a ruthenium complex.

6. The process as claimed in claim 2, wherein the metathesis catalyst (3) used is a ruthenium complex of the formula $RuCl_2$ (=CHPh) $(PCy_3)_2$, where Ph is a phenyl radical, and Cy is a cyclohexyl radical.

7. The process as claimed in claim 3, wherein the metathesis catalyst (3) used is a ruthenium complex of the formula $RuCl_2$ (=CHPh) $(PCy_3)_2$, where Ph is a phenyl radical, and Cy is a cyclohexyl radical.

8. The process as claimed in claim 4, wherein the metathesis catalyst (3) used is a ruthenium complex of the formula $RuCl_2$ (=CHPh) $(PCy_3)_2$, where Ph is a phenyl radical, and Cy is a cyclohexyl radical.

9. The process as claimed in claim 2, wherein the α-olefin (2) used is ethylene.

10. The process as claimed in claim 3, wherein the α-olefin (2) used is ethylene.

11. The process as claimed in claim 4, wherein the α-olefin (2) used is ethylene.

12. The process as claimed in claim 5, wherein the α-olefin (2) used is ethylene.

13. The process as claimed in claim 6, wherein the α-olefin (2) used is ethylene.

14. The process as claimed in claim 2, wherein the metathesis catalyst (3) used is a ruthenium complex of the formula $RuCl_2$ (=CH—CH=CPh_2) $(PCy_3)_3$, where Ph is a phenyl radical, and Cy is a cyclohexyl radical.

15. The process as claimed in claim 3, wherein the metathesis catalyst (3) used is a ruthenium complex of the formula $RuCl_2$ (=CH—CH=CPh_2) $(PCy_3)_3$, where Ph is a phenyl radical, and Cy is a cyclohexyl radical.

16. The process as claimed in claim 4, wherein the metathesis catalyst (3) used is a ruthenium complex of the formula $RuCl_2$ (=CH—CH=CPh_2) $(PCy_3)_3$, where Ph is a phenyl radical, and Cy is a cyclohexyl radical.

17. The process as claimed in claim 5, wherein the metathesis catalyst (3) used is a ruthenium complex of the formula $RuCl_2$ (=CH—CH=CPh_2) $(PCy_3)_3$, where Ph is a phenyl radical, and Cy is a cyclohexyl radical.

18. The process of claim 2 wherein B is selected from the group consisting of 3-cyclohexenyl, 4-cyclooctenyl, 5-norbornenyl, 2-(5-norbornenyl)ethyl-, 2(3)-dicyclopentadienyl radicals, and mixtures thereof.

19. The organosilicon compound of claim 1, wherein A is a radical of the formula:

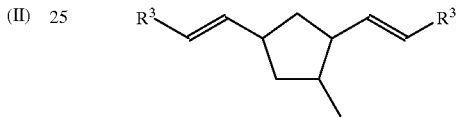

where $R^3$ is a hydrogen or a $C_{1-20}$ hydrocarbon free of carbon-carbon multiple bonds.

20. An α, ω-substituted polyorganosiloxane having as the α, ω substituents, two radicals of the formula:

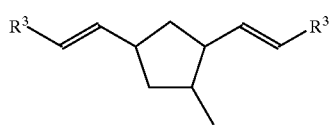

where $R^3$ is a hydrogen or a $C_{1-20}$ hydrocarbon free of carbon-carbon multiple bonds.

21. The process of claim 1 wherein said organosilicon compound has at least two radicals A per molecule.

22. The process of claim 2 wherein said organosilicon compound (1) is a polydiorganosiloxane having α,ω-terminal groups of the formula (II) where a is 1 in each terminal group.

23. The process of claim 1, further comprising equilibrating said organosilicon compound containing alkenyl groups and comprising units of the formula (I) with an organopolysiloxane.

24. The process of claim 23 wherein said organopolysiloxane used in said step of equilibrating comprises at least one organopolysiloxane selected from the group consisting of linear triorganosiloxy-terminated organopolysiloxanes of the formula

$$R_3SiO(R_2SiO)_rSiR_3$$

where R is as defined above and r is 0 or an integer from 1 to 1000, and linear, hydroxyl-terminated organopolysiloxanes of the formula

$$HOR_2SiO(R_2SiO)_rSiR_2OH.$$

25. The process of claim 23 wherein r is from 100 to 400.

* * * * *

UNITED STATES PATENT AND TRADEMARK OFFICE
CERTIFICATE OF CORRECTION

PATENT NO. : 6,252,101 B1
DATED : June 26, 2001
INVENTOR(S) : Christian Herzig et al.

It is certified that error appears in the above-identified patent and that said Letters Patent is hereby corrected as shown below:

Column 11, claim 2,
Line 38, delete "α-olefms" and insert -- α-olefins --.

Signed and Sealed this

Fourth Day of December, 2001

Attest:

*Nicholas P. Godici*

NICHOLAS P. GODICI
*Attesting Officer*        *Acting Director of the United States Patent and Trademark Office*